(12) United States Patent
Hope Simpson et al.

(10) Patent No.: US 11,324,485 B2
(45) Date of Patent: May 10, 2022

(54) ULTRASOUND IMAGING SYSTEM WITH A NEURAL NETWORK FOR DERIVING IMAGING DATA AND TISSUE INFORMATION

(71) Applicant: KONINKLIJKE PHILIPS N.V., Eindhoven (NL)

(72) Inventors: David Hope Simpson, Bothell, WA (US); Earl M. Canfield, Snohomish, WA (US); Robert Gustav Trahms, Edmonds, WA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 376 days.

(21) Appl. No.: 16/474,319

(22) PCT Filed: Jan. 3, 2018

(86) PCT No.: PCT/EP2018/050086
§ 371 (c)(1),
(2) Date: Jun. 27, 2019

(87) PCT Pub. No.: WO2018/127497
PCT Pub. Date: Jul. 12, 2018

(65) Prior Publication Data
US 2019/0336108 A1 Nov. 7, 2019

Related U.S. Application Data

(60) Provisional application No. 62/522,134, filed on Jun. 20, 2017, provisional application No. 62/442,691, filed on Jan. 5, 2017.

(51) Int. Cl.
*A61B 8/08* (2006.01)
*G06T 7/00* (2017.01)
(Continued)

(52) U.S. Cl.
CPC .......... *A61B 8/5223* (2013.01); *A61B 8/0891* (2013.01); *A61B 8/13* (2013.01);
(Continued)

(58) Field of Classification Search
CPC ....... A61B 8/0891; A61B 8/13; A61B 8/5207; A61B 8/5223; G06T 2207/10132;
(Continued)

(56) References Cited

U.S. PATENT DOCUMENTS

2009/0270731 A1* 10/2009 Sathyanarayana ....... A61B 8/08
600/443
2015/0080725 A1* 3/2015 Wegner ............... G01S 15/8997
600/440

(Continued)

FOREIGN PATENT DOCUMENTS

EP 2434454 A2 3/2012

OTHER PUBLICATIONS

International Search and Written Opinion for International Application No. PCTEP2018/050086, filed Jan. 3, 2018, 15 pages.

*Primary Examiner* — Amelie R Davis

(57) ABSTRACT

An ultrasound system according to some embodiments may include an ultrasound transducer configured to transmit ultrasound pulses toward tissue and generate echo signals responsive to the ultrasound pulses, a channel memory configured to store the echo signals, a beamformer configured to generated beamformed signals responsive to the echo signals, a neural network configured to receive one or more samples of the echo signals or the beamformed signals and produce a first type of ultrasound imaging data, and a processor configured to generate a second type of ultrasound imaging data, wherein the one or more processors may be further configured to generate an ultrasound image based on the first type of ultrasound imaging data and the second type (Continued)

of ultrasound imaging data and to cause a display communicatively coupled therewith to display the ultrasound image.

20 Claims, 6 Drawing Sheets

(51) Int. Cl.
*A61B 8/13* (2006.01)
*G01S 7/52* (2006.01)

(52) U.S. Cl.
CPC ........ *A61B 8/5269* (2013.01); *G01S 7/52036* (2013.01); *G06T 7/0012* (2013.01); *G06T 2207/10132* (2013.01); *G06T 2207/20081* (2013.01); *G06T 2207/20084* (2013.01); *G06T 2207/30004* (2013.01)

(58) Field of Classification Search
CPC . G06T 2207/20081; G06T 2207/20084; G06T 2207/30004; G06T 7/0012
See application file for complete search history.

(56) References Cited

U.S. PATENT DOCUMENTS

2016/0350620 A1 12/2016 Rao et al.
2018/0075597 A1* 3/2018 Zhou ..................... G06N 20/00
2018/0125446 A1* 5/2018 Boroczky .......... A61B 10/0241

* cited by examiner

ULTRASOUND IMAGING SYSTEM WITH A NEURAL NETWORK FOR DERIVING IMAGING DATA AND TISSUE INFORMATION

RELATED APPLICATIONS

This application is the U.S. National Phase application under 35 U.S.C. § 371 of International Application No. PCT/EP2018/050086, filed on Jan. 3, 2018, which claims the benefit of both Provisional Application Ser. No. 62/522,134, filed Jun. 20, 2017, and Provisional Application Ser. No. 62/442,691, filed Jan. 5, 2017. These applications are hereby incorporated by reference herein.

TECHNICAL FIELD

The present disclosure pertains to ultrasound systems and methods which utilize a neural network for deriving imaging data, tissue information and diagnostic information from raw ultrasound echoes.

BACKGROUND

Ultrasound is a widely used imaging modality in medical imaging as it can provide real-time non-invasive imaging of organs and tissue for diagnosis, pre-operative care and planning, and post-operative patient monitoring. In a conventional ultrasound imaging system, a transducer probe transmits ultrasound toward the tissue to be imaged and detects echoes responsive to the ultrasound. Acquired echo signals (also referred to as radio frequency or RF signals) are passed through a series of signal processing components, including for example a beamformer which combines raw channel data (e.g., RF signals from multiple transducer elements) or partially beam-formed signals of patches of transducer elements into fully beamformed signals, a demodulator which extracts quadrature signals from the beamformed signals, and one or more filters, to produce image data (e.g., pixel information that may be used to produce a 2D or 3D ultrasound image). In addition to providing an ultrasound image of the anatomy, existing ultrasound system may be configured to perform a variety of other types of processing to extract additional information from the echo signals. For examples, many ultrasound systems are configured to process the beamformed signals, typically in parallel with processing for anatomy image formation, for extraction of Doppler data in order to provide flow information. To do so, conventional systems may utilize a particularly configured signal processor to derive the Doppler frequency from a plurality of temporally spaced samples of the echo signals. Other systems may be configured to perform elastography, vector flow imaging, and other types of imaging as may be desirable for a variety of clinical applications. For these purposes, conventional systems may include particularized hardware components (e.g., pre-programmed processors) which are designed to perform a specific sequence of signal and image processing steps.

As such, conventional ultrasound system, while providing a significant advancement in medical imaging, may still benefit from further improvements. For example, conventional signal processing components rely on and implement model-based algorithms, some of which may be imperfect and thus only provide approximations. Limitations of pre-programmed algorithms, as well as hardware limitations, may introduce image artifacts or other shortcomings in the output of a conventional system. The hard-wiring or pre-programming of specific models or signal processing paths into a system may render it less flexible for future improvements and adaptation to the needs of a user. Therefore, improvements in this area may be desirable. Also, current ultrasound systems generally require the user to carefully watch the ultrasound system display, coordinate transducer movements and manipulate user controls to precisely record the desired anatomy or pathology of interest. After capturing the desired images the user will typically review the images and manually annotate specific anatomy or pathology. Techniques for simplifying operation of an ultrasound imaging system without sacrificing image and/or diagnostic information quality may thus also be desirable.

SUMMARY

The present disclosure pertains to ultrasound systems and methods which utilize a neural network (e.g., a machine-trained algorithm or hardware implemented network of artificial neurons or nodes) for deriving imaging data and/or a variety of other tissue information, such as tissue type characterization information, qualitative or quantitative diagnostic information, and other types of clinically relevant information) from raw ultrasound echo signals or from fully or partially beam-formed RF signals. In some embodiments, the neural network may be a deep neural network capable of analyzing patterns using a with a multi-dimensional (2- or more dimensional) data set, which may also be thought of as a localized data sets, and where the location of data within the data set and the data values may both contribute to the analyzed result.

An ultrasound system according to some embodiments may include an ultrasound transducer configured to transmit ultrasound pulses toward tissue and generate echo signals responsive to the ultrasound pulses, a channel memory configured to store the echo signals, a beamformer configured to generated beamformed signals responsive to the echo signals, a neural network configured to receive one or more samples of the echo signals or the beamformed signals and produce a first type of ultrasound imaging data, and a processor configured to generate a second type of ultrasound imaging data, wherein the one or more processors may be further configured to generate an ultrasound image based on the first type of ultrasound imaging data and the second type of ultrasound imaging data and to cause a display communicatively coupled therewith to display the ultrasound image.

In some embodiments, the ultrasound imaging system may be configured to produce B-mode imaging data as the second type of imaging data, and to produce Doppler imaging data, vector flow imaging data, elastography imaging data, tissue type characterization data, wall shear stress of an anatomical structure containing a fluid therein, tissue composition data, ultrasound contrast agent information, plaque characterization data, one or more diagnostic indicators associated with the B-mode imaging data, or any combinations thereof as the first type of imaging data.

In some embodiments, the neural network may include a deep neural network (DNN) or a convolutional neural network (CNN). In some embodiments, the neural network may be implemented in hardware, software, or a combination thereof. For example, the neural network may be implemented, at least in part, in a computer-readable medium comprising executable instructions, which when executed by a neural network processor coupled to the channel memory, the beamformer, or both, cause the neural network processor to perform a machine-trained algorithm to produce the first type of ultrasound imaging data responsive to the one or more samples of the echo signals or the beamformed signals.

In some embodiments, the neural network may include a data selector configured to select samples of the stored echo signals or the beamformed signals as input to the neural network. In some embodiments, the data selector may be configured to selectively couple either samples of echo signals or samples of beamformed signals to the neural network responsive to a control signal received by the data selector. In some embodiments, the control signal may be generated responsive to user input such as to enable the user to select the type of input provided and corresponding operational mode of the neural network. In some embodiments, the neural network may be configured to additionally receive auxiliary data as input and the auxiliary data may include ultrasound transducer configuration information, beamformer configuration information, information about the medium, or combinations thereof. In such embodiments, the first type of imaging data may be estimated by the neural network further based on the auxiliary data.

In some embodiments, the neural network may be operatively associated with a training algorithm configured to receive an array of training inputs and known outputs, wherein the training inputs comprise echo signals, beamformed signals, or combinations thereof associated with a region of imaged tissue and the known outputs comprise known properties of the region of imaged tissue. In some embodiments, the training algorithm may be configured to utilize, with training inputs comprising ultrasound data, known outputs obtained using an imaging modality other than ultrasound. In some embodiments, the neural network may be configured to process the input data in accordance with one of a plurality of operational modes, which may be selected responsive to user input or automatically set by the ultrasound system based on an imaging mode of the ultrasound system during acquisition of the echo signals. In some embodiments, the neural network may be configured to predict a fat content of the tissue based on the input data without use of the second type of imaging data. In some embodiments, the neural network may be configured to predict flow properties of a fluid contained in an anatomical structure of the tissue based on temporally successive samples of the input data without the use the quadrature signals produced by the image processing circuit. In some embodiments, the neural network may be configured to produce predicted beamformed signals based on samples of the echo signals, and to use the predicted beamformed signals to generate the first type of imaging data.

A method of ultrasound imaging in accordance with some embodiments may include generating echo signals responsive to ultrasound transmitted by a transducer operatively coupled to an ultrasound system, storing the echo signals in channel memory, beamforming a plurality of the echo signals from the channel memory to produce beamformed signals, coupling samples of the echo signals, the beamformed signals, or a combination thereof, to a neural network trained to output a first type of imaging data responsive to the samples of the echo signals or the beamformed signals, coupling the beamformed signals to a processor configured to generate a second type of imaging data responsive to the beamformed signals, and generating an ultrasound image based on the first type of imaging data and the second type of imaging data. One or more frames of ultrasound images generated responsive to both the first type and second type of imaging data may be provided to a display, to storage (e.g., persistent storage or a cineloop memory), or another type of output device for real-time use or subsequent use (e.g., in subsequent training of the neural network). In some embodiments, the second type of imaging data may be B-mode imaging data and the first type of imaging data may include flow imaging data, tissue stiffness imaging data, wall shear stress of an anatomical structure containing a fluid therein, tissue composition data, ultrasound contrast agent information, plaque characterization data, one or more diagnostic indicators associated with the B-mode imaging data, or combinations thereof.

In some embodiments, coupling samples of the echo signals, the beamformed signals, or a combination thereof to the neural network may include coupling an input (e.g., an array) comprising samples of the echo signals or samples of the beamformed signals corresponding to a location within a region of imaged tissue to the neural network and propagating the input through the neural network to estimate pixel data associated with the location within the region of imaged tissue. In some embodiments, coupling samples of the echo signals, the beamformed signals, or a combination thereof to the neural network may include coupling to the neural network an input comprising samples of echo signals or samples of beamformed signals from temporally sequential transmit and receive cycles received from a location within a region of imaged tissue and propagating the input through the neural network to estimate a velocity of flow at the location. In some embodiments, the method may include selectively coupling, responsive to user input, either samples of the echo signals or samples of the beamformed signals as input data to the neural network, and selecting a corresponding operational mode of the neural network based on the input data. In some embodiments, the method may further include training the neural network. For example, the method may include providing at least some of the second type of imaging data to the neural network during a training mode of the neural network. In some embodiments, the method may further include training the neural network using imaging data obtained by an imaging modality other than ultrasound.

Any of the methods described herein, or steps thereof, may be embodied in non-transitory computer-readable medium comprising executable instructions, which when executed may cause a processor of a medical imaging system to perform method or steps embodied therein.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound system according to the present disclosure may utilize a neural network, for example a deep neural network (DNN), a convolutional neural network (CNN) or the like, to bypass certain processing steps in conventional ultrasound imaging. In some examples, the neural network may be trained using any of a variety of currently known or later developed machine learning techniques to obtain a neural network (e.g., a machine-trained algorithm or hardware-based system of nodes) that is able to derive or calculate the characteristics of an image for display from raw channel data (i.e., acquired radio frequency (RF) echo signals) or in some cases, from partially- or fully-beamformed signals. Neural networks may provide an advantage over traditional forms of computer programming algorithms in that they can be generalized and trained to recognize data set features by analyzing data set samples rather than by reliance of specialized computer code. By presenting appropriate input and output data to a neural network training algorithm, the neural network of an ultrasound system according to the present disclosure can be trained to produce image data (e.g., flow imaging data) and derive other types of tissue information (e.g., tissue content or type, strain/stress data, identification of specific anatomical structures, within the imaged region, etc.) without the need for a physically-derived model to guide system operation.

Figure 1:
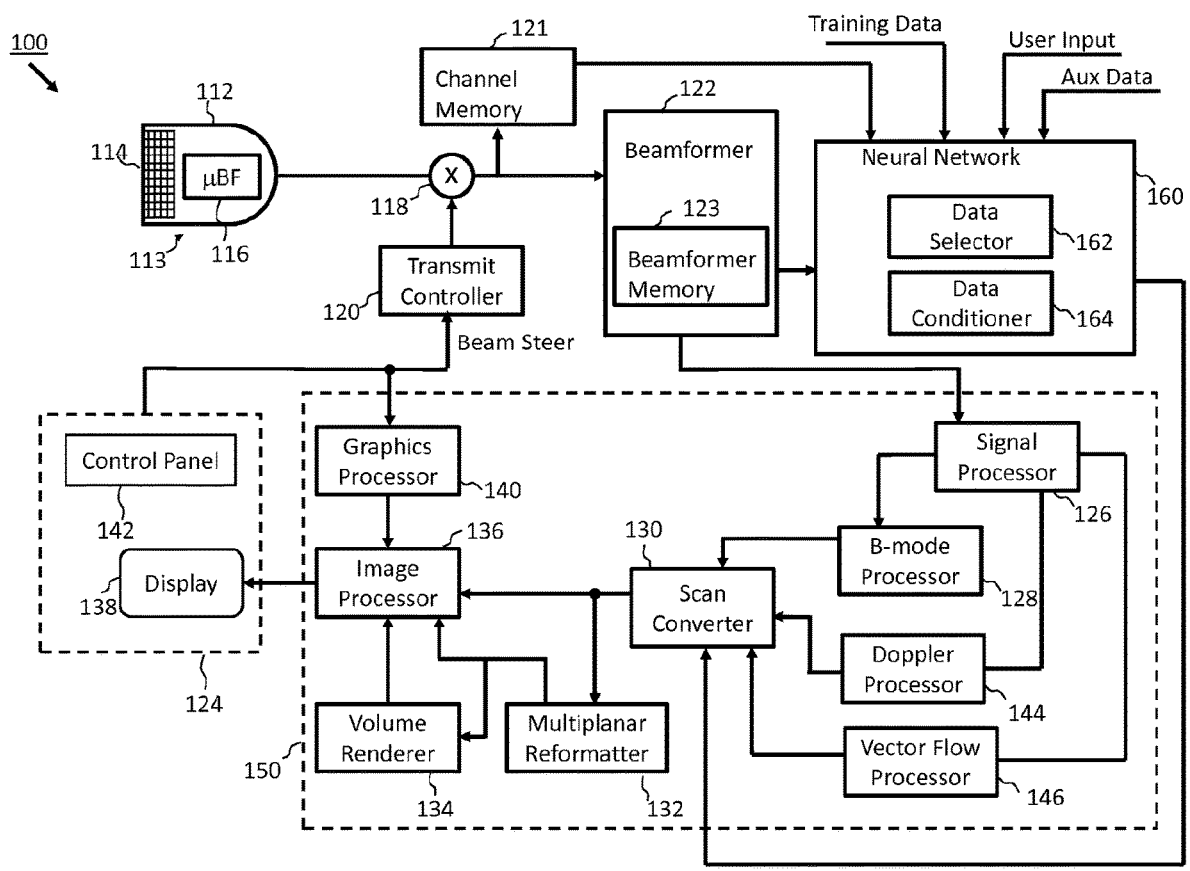
FIG. 1 shows a block diagram of an ultrasound system in accordance with principles of the present inventions.

FIG. 1 shows an example ultrasound system in accordance with principles of the present invention. The system 100 may include or be operatively coupled to an ultrasound transducer 113 configured to transmit ultrasound pulses toward a medium and generate echo signals responsive to the ultrasound pulses. The ultrasound system 100 may include channel memory 121 configured to store the acquired echo signals (raw RF signals), and a beamformer 122, which may be configured to perform transmit and/or receive beamforming and which may include a beamformer memory 123 configured to store beamformed signals generated responsive to the acquired echo signals. In some embodiments, the system 100 may include or be communicatively coupled to a display 138 for displaying ultrasound images generated by the ultrasound system 100.

The ultrasound transducer 113 may include an ultrasound transducer array 114, which may be provided in a probe 112, for example a hand-held probe or a probe configured to be at least partially controlled by a computer (e.g., a machine-actuated probe). In some examples, the array 114 may be implemented using a plurality of patches, each comprising a sub-array of transducer elements and the array 114 may be configured to be conformably placed against the subject to be imaged. The array 114 is operable to transmit ultrasound toward a region of interest and to receive echoes for imaging the region of interest (ROI). A variety of transducer arrays may be used, e.g., linear arrays, curved arrays, or phased arrays. The array 114 may include, for example, a two dimensional array of transducer elements capable of scanning in both elevation and azimuth dimensions for 2D and/or 3D imaging.

The array 114 may be coupled to a microbeamformer 116, which may be located in the probe 112 or in an ultrasound system base (e.g., in a cart-based system such as the SPARQ or EPIQ ultrasound system provided by Philips. The microbeamformer 116 may control the transmission and reception of signals by the array 114. The array 114 may be coupled to the ultrasound system base via the microbeamformer 116, which may be coupled (via a wired or wireless connection) to a transmit/receive (T/R) switch 118 typically located in the base. The T/R switch 118 may be configured to switch between transmission and reception, e.g., to protect the main beamformer 122 from high energy transmit signals. In some embodiments, the functionality of the T/R switch 118 and other elements in the system may be incorporated within the probe, such as a probe operable to couple to a portable system, such as the LUMIFY system provided by PHILIPS. The probe 112 may be communicatively coupled to the base using a wired or wireless connection. The probe 412 may be communicatively coupled to the base using a wired or wireless connection. In some embodiments, the transducer, the channel memory, and hardware storing the neural network can be located in the probe, and a display for displaying images created by the neural network can be communicatively coupled to the probe. For example, the display can be coupled via a cable to the probe or via wireless communication, in which the probe can include a wireless transmitter to send the image data to the display. In certain embodiments, the system can include a graphics processing unit (GPU) to fully or partially train the neural network in the system. For example, a GPU can be located in a probe with the transducer, the channel memory and the hardware storing the neural network. Alternatively, the GPU can be located separately from the probe, such as being located in a tablet or other computing device, such as a smart phone.

The ultrasound transducer 113 may be configured to acquire echo signals responsive to ultrasound signals transmitted toward a medium to be imaged (e.g., tissue). As described, the transducer 113 may include an array of elements capable, under control from the transmit/receive controller 120, to transmit pulses of ultrasound toward the medium and detect echoes responsive to the transmit pulses. The transmit/receive controller 120 controls the transmission of ultrasound signals by the transducer 113 and the reception of ultrasound echo signals by individual elements or groups of elements of the array (e.g., in the case of a transducer including a microbeamformer (μBF) 116). The transmit/receive controller 120, in controlling the transmission and reception of signals, may receive input from the user's operation of a user interface 124. The user interface 124 may include one or more input devices such as a control panel 142, which may include one or more mechanical controls (e.g., buttons, encoders, etc.), touch sensitive controls (e.g., a trackpad, a touchscreen, or the like), and other input devices. Another function which may be controlled by the transmit/receive controller 120 is the direction in which beams are steered. Beams may be steered straight ahead from (orthogonal to) the transmission side of the array 114, or at different angles for a wider field of view. Echo signals received by the ultrasound transducer 113 may be coupled to channel memory 110, which receives and stores the acquired echo signals. The channel memory 110 may be configured to store per-element or group (in the case of microbeamformed signals) echo signals (also referred to as raw RF signals or simply RF signals, or per-channel data). The pre-channel data may be accumulated in memory over multiple transmit/receive cycles.

Figure 2:
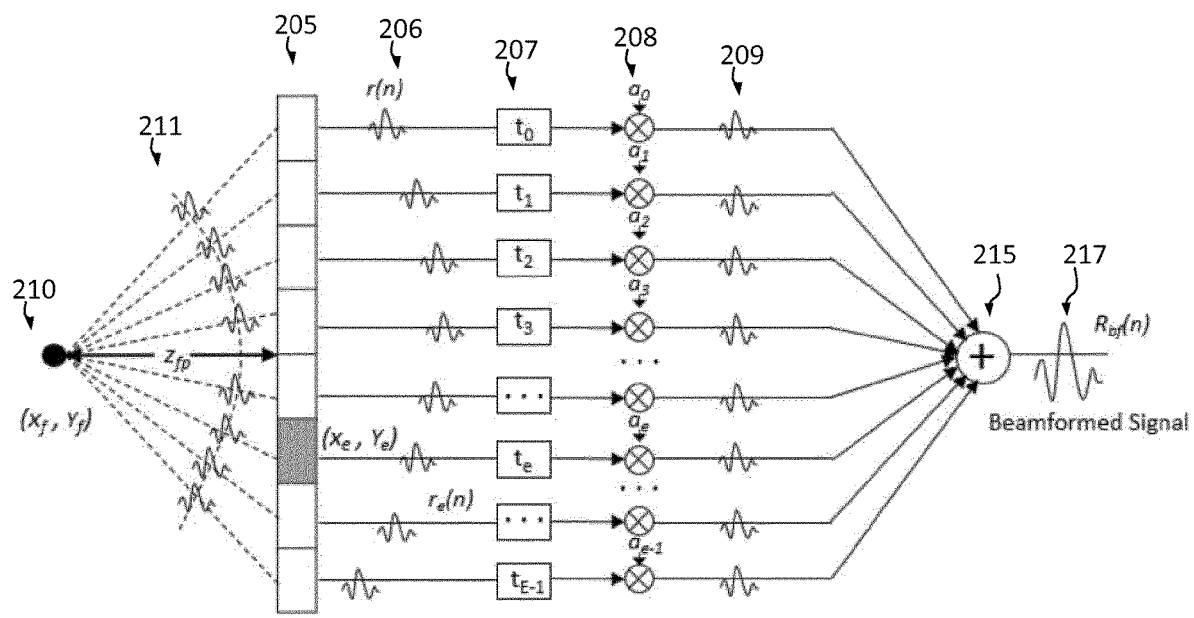
FIG. 2 shows a delay and sum beamforming technique.

The system 100 may further include a beamformer 122, which is configured to receive the acquired echo signals and produce beamformed RF signals. The beamformer 122 may combine individual echo signals or partially beamformed signals from groups of transducer (e.g., in the case of a transducer associated with a microbeamformer) into a fully beamformed signal. For example, the beamformer 122 may perform delay and sum beamforming as shown in FIG. 2. As shown in FIG. 2, the beamformer (e.g., beamformer 122) may receive per-channel RF signals 206, which correspond to echoes 211 from a reflector 210 as detected by elements 205 of the array. The raw RF signals 206 are delayed by an appropriate amount of time 207 to temporally align them (as shown at 209) and then combined (as shown at 215) into a beamformed signal 217, which may also be referred to as beamformed RF signal or summed RF signal. In some cases, the temporally aligned signals may be multiplied by a factor (as shown at 208) before they are summed. In some cases, a microbeamformer may be included, for example in the transducer probe, which performs partial beamforming of signals received by patches of elements (e.g., a subset of the elements detecting echoes in any given transmit/receive cycle) and thereby reduces the number of channel inputs into the main beamformer. In such cases, the main beamformer (e.g., beamformer 122) may produce fully beamformed signals corresponding to a scan line within the field of view from the partially beamformed signals. In some embodiments, the beamformer (and/or microbeamformer, if included) may be configured to use, alternatively or additionally, other techniques, including but not limited to, dual apodization with cross-correlation, phase coherence imaging, capon beamforming and minimum variance beamforming, all operating on the per-channel data to combine the information from the echo signals and form an image line of the backscattered ultrasound energy from tissue.

Referring back to FIG. 1, the beamformed signals produced by the beamformer may be coupled to further downstream signal processing components (e.g., processor 150) for generating one or more types of ultrasound imaging data, for example imaging data for producing a grayscale image of the scanned anatomy (e.g., a B-mode image). The processor 150 may be implemented in software and hardware components including one or more CPUs, GPUs, and/or ASICs specially configured to perform the functions described herein for generating ultrasound images and providing a user interface for display of the ultrasound images. In some embodiments, samples of the beamformed signals may, alternatively or additionally, be coupled to the neural network 160, which may be trained to produce one or more other types of imaging data such as flow imaging data, tissue elasticity imaging data, and others. The imaging data produced by the processor 150 may be used to generate an ultrasound image which also includes imaging data output from the neural network 160, e.g., as described further below. In some embodiments, the beamformed signals may be stored in beamformer memory 123, over one or multiple transmit/receive cycles, until they are used for image generation (e.g., by the neural network and/or by the one or more image processors) or tissue characterization.

As shown in the example in FIG. 1, the system 100 may include one or more processing components, collectively referred to as processor 150, which is configured to receive beamformed signals and generate one or more types of imaging data for producing an ultrasound image (e.g., a B-mode image). For example, the beamformed signals may be coupled to a signal processor 126, which is configured to process the beamformed signals in various ways, such as by bandpass filtering, decimation, I and Q component separation, and harmonic signal separation. The signal processor 126 may also perform additional signal enhancement such as speckle reduction, signal compounding, and noise elimination. The processed signals may be coupled to a B-mode processor 128 for producing B-mode imaging data. The B-mode processor 128 can employ amplitude detection for the imaging of structures in the body. The signals produced by the B-mode processor 128 may be coupled to a scan converter 130 and a multiplanar reformatter 132. The scan converter 130 may be configured to arrange the signals in the spatial relationship from which they were received in a desired image format. For instance, the scan converter 130 may arrange the signals into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). A volume renderer 134 may generate an image of the 3D dataset as viewed from a given reference point, e.g., as described in U.S. Pat. No. 6,530,885 (Entrekin et al.).

Additionally and optionally, signals from the signal processor 126 may be coupled to a Doppler processor 144, which may be configured to estimate the Doppler shift and generate Doppler image data. The Doppler image data may include colorflow data which may be overlaid with B-mode (or grayscale) image data for displaying a conventional duplex B-mode/Doppler image. In some examples, the Doppler processor 144 may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, may then be coupled the scan converter 130 where the Doppler image data is converted to the desired image format and overlaid on the B-mode image of the tissue structure containing the blood flow to form a color Doppler image.

Additionally and optionally, the system 100 may include a vector flow processor 146, which may be configured to extract beam-angle-independent velocity information from the signals generated responsive to the detected echoes. For example, the vector flow processor 146 may be configured to estimate the beam-angle-independent velocity components of flow within an imaged bodily structure (e.g., a blood vessel) using the transverse oscillation method or synthetic aperture method (e.g., as described by Jensen et al., in "Recent advances in blood flow vector velocity imaging," 2011 IEEE International Ultrasonics Symposium, pp. 262-271, the disclosure of which is incorporated herein by reference in its entirety for any purpose), or any other currently known or later developed vector flow estimation and imaging technique.

Similar to the imaging data from the B-mode processor, the imaging data produced by any of these additional optional image data processors may be coupled to the scan converter 130 for arranging the signals in the spatial relationship from which they were received in a desired image format (e.g., a two dimensional (2D) sector-shaped format, or a pyramidal or otherwise shaped three dimensional (3D) format) and to the multiplanar reformatter 132 for extracting a set of the signals received from points in a common plane in a volumetric region of the body into an ultrasonic image of that plane. In the case of 3D imaging, the signals may additionally or alternatively be coupled to the volume renderer 134 may generate an image of the 3D dataset as viewed from a given reference point. Thus, it will be understood that the processor 150 may include one or more signal processing paths, circuits, or specifically programmed software components to produce B-mode imaging data, Doppler imaging data, vector flow imaging (VFI) data, etc. as may be desired, which data may be arranged in a desired display format including combining the data for duplex (e.g., an overlay of Doppler and B-mode data or of B-mode and stress/strain data) or triplex displays (e.g., an overlay of Doppler and B-mode in one image window concurrently displayed with a second image window showing a graphical display such as an M-mode image or a spectral Doppler image).

In accordance with principles of the present invention, the system 100 may include a neural network 160. The neural network 160 may be configured to receive one or more samples of the echo signals, one or more samples of the beamformed signals, or a combination thereof, as input and produce another type of ultrasound imaging data responsive to the input. The neural network 160 may be implemented in hardware (e.g., using hard-wired circuitry for the artificial nodes of the network) and/or software components (e.g., using executable instructions which program one or more processors to implement a machine-trained algorithm). The neural network 160 may be trained to propagate the input (e.g., samples of raw echo signals and/or samples of beamformed signals) through the network of nodes to obtain predicted or estimated imaging data, which may subsequently be further processed for display. In some cases the network may be trained to operate in any one of a plurality of operational modes and may produce, responsive to the same input, a different type of imaging data or output other tissue information depending on the operational mode of the network. The mode may be selective (e.g., responsive to user input, or automatically selected by the system).

As described, the neural network 160 may be hardware- (e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer-readable medium, and which when executed cause the processor to perform a machine-trained algorithm for producing ultrasound images and/or outputting tissue information from one or more of the above identified inputs. The ultrasound system may include a display or graphics processor, which is operable to arrange the ultrasound image and/or additional graphical information, which may include annotations, tissue information, which may also be output by the neural network, and other graphical components, in display window for display on the display of the ultrasound system. In some embodiments, the ultrasound images and tissue information may additionally be provided to a storage device, such as a picture archiving and communication system (PACS) or another local or remote/networked storage device, for reporting purposes or future machine training (e.g., to continue to enhance the performance of the neural network). In yet further examples, imaging data obtained from a variety of different imaging modalities (e.g., magnetic resonance imaging (MRI), computed tomography (CT), or another), which may be stored in PACS, may alternatively or additionally be used to train the neural network. As will be appreciated, systems according to the present disclosure may include a two-way communication link coupling the system, and more specifically the neural network to source(s) of training data (e.g., a storage device) and/or to other machine-trained systems for ongoing feedback and training.

In some embodiments, the neural network 160 may be configured specifically to produce imaging data and/or any desired tissue information other than B-mode imaging data. For example, the neural network may be trained to provide flow imaging data (e.g., beam-angle dependent or beam-angle independent velocity information) directly from the echo signals and/or beamformed signals, while the system produces an anatomy image for overlay therewith using the pre-programmed or model-based processing components in processor 150. The B-mode imaging data may then be combined (in this case, overlaid) with the flow imaging data to produce an ultrasound image similar to a conventional Doppler image showing a color-coded flow map (or in the case of VFI, showing a vector field) onto a grayscale anatomy image. In other embodiments, the neural network may be trained to provide elastography imaging data (e.g., tissue stiffness information) directly from the echo signals and/or beamformed signals, while the system produces an anatomy image for overlay therewith using the pre-programmed or model-based processing components in processor 150. In conventional elastography, the tissue stiffness information is color coded similar to how flow information may be color coded for display. In the current example, the elastography imaging data (e.g., tissue stiffness information) may be coupled to the processor 150 (e.g., to the scan converter and the multiplanar reformatter or volume renderer) to arrange the tissue stiffness information in a desired format for display with the anatomy image produced based on B-mode data output by the B-mode processor. Other types of imaging data and/or tissue information may be estimated directly from the echo signals and/or beamformed signals by the neural network bypassing standard image formation techniques and reliance on downstream signal processing. In this manner, the imaging data and/or tissue information output by the neural network may not be negatively affected by image artefacts and may thus be more accurate, especially with further training of the neural network over time. The use of a neural network for generating imaging data and tissue information in a variety of clinical applications, some of which are described further below, may be implemented in accordance with the examples herein.

Figure 3:
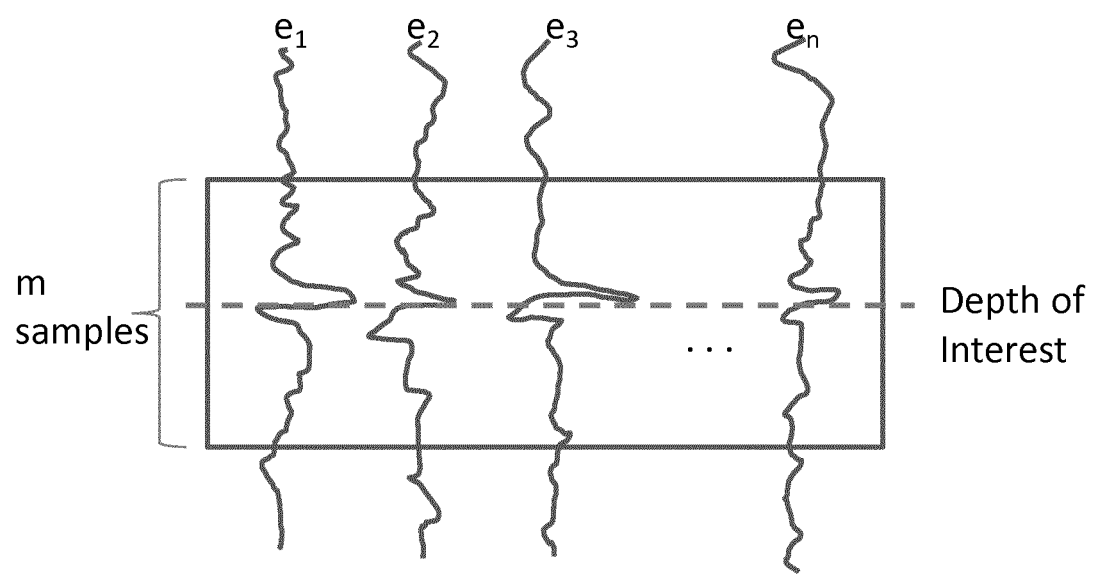
FIG. 3 shows aspects of input data selection for a neural network in accordance with principles of the present inventions.

To train a neural network 160 according to the present disclosure, training sets which include multiple instances of input arrays and output classifications, {Xi,Yn}, may be presented to the training algorithm(s) of the neural network 160 (e.g., an AlexNet training algorithm, as described by Krizhevsky, A., Sutskever, I. and Hinton, G. E. "*ImageNet Classification with Deep Convolutional Neural Networks*," NIPS 2012 or its descendants). In the training data set, the input data [Xi] may include per-channel echo signals, e.g., as illustrated in FIG. 3, optionally together with auxiliary data, described further below, and the output data [Yi] may include any known properties of the tissue corresponding to the sample of echo signals (e.g., known velocities in the case of blood flow or other tissue motion imaging, known strain/stress values, or echo intensity data for producing anatomy imaging information, etc.). The input [Xi] and output [Yi] data of the training data sets may be acquired by an ultrasound imaging system which has components for conventional ultrasound imaging or an imaging system configured for another type of imaging modality (e.g., an MRI scanner, CT scanner, and others). In some embodiments the system 100 may also include conventional beamforming, signal and image processing components to acquire input and output data sets for use in producing combined images or for providing additional training sets to the training algorithm associated with neural network 160. For example, different types of tissue may be scanned (e.g., ultrasonically scanned) using a transducer which is operatively associated with a spatial localization system (e.g., an EM or ultrasonically tracked probe), which can spatially correlate the point or region of interest of tissue being scanned to the output data (e.g., the imaging data and/or tissue characterization information to be used as the output in the training set). In further examples, the neural network 160 may be trained using a suitable ultrasound simulation such as the Field II program (as described by J. A. Jensen: *A Model for the Propagation and Scattering of Ultrasound in Tissue*, J. Acoust. Soc. Am. 89, pp. 182-191, 1991), which takes as input the spatial distribution of points representing scatterers in an image field together with data about the geometry of the ultrasound transducer and the transmitted pulse and outputs computed ultrasonic data representing the per-element echo signals (also referred to as simulated echoes). The system 100 may use this type of data for training purposes, e.g., by using the simulated echoes and auxiliary data about the transducer and transmitted pulses for one or more given points in space and present them to the neural network as input training data [Xi] with the corresponding output data [Yi] being the scatterer densities from the simulation. Other algorithms or techniques may additionally or alternatively be used for training the neural network 160. Also, as noted, in some cases, the output data (e.g., imaging data and/or known properties of tissue) may be obtained using an imaging modality different from ultrasound, for example MRI, CT or others or any combinations thereof. The neural network 160 may thus be trained to produce imaging data, and in some case images of higher quality (e.g., higher resolution) than may otherwise be possible through conventional ultrasound image processing directly from the RF signals.

A neural network training algorithm associated may be presented with thousands or even millions training data sets in order to train the neural network 160 to directly estimate or output imaging data or a variety of tissue properties based on the raw measurement data (i.e., raw echo or beamformed RF signals) without reliance on an explicit model of the input/output relationship (e.g., pre-programmed physics-based models typically implemented in conventional beamformers, signal processors or imaging data processors of existing ultrasound systems). That is, hundreds, thousands, or millions of training data sets may be presented to a machine learning algorithm to develop a network of artificial neurons or nodes arranged in accordance with any one of a variety of topographies or models. The neurons of the neural network are typically connected in layers and signals travel from the first (input) layer to the last (output) layer. With advancements in modern neural networks and training algorithms, a neural network comprising hundreds of thousands to millions of neurons or nodes and connections therebetween may be developed. The signals and state of the artificial neurons in a neural network 160 may typically be real numbers, typically between 0 and 1, and a threshold function or limiting function may be associated with each connection and/or node itself, such that the signal must equal or exceed the threshold/limit before propagating.

The output of the training process may be a set of weights (also referred to as connection or node weights) which may be used by the neural network 160 during operation (e.g., to adjust the threshold or limiting functions controlling propagation through the layers of the neural net). Once trained, the neural network 160 may be configured to operate on any input array, Xk, to produce one or more output values that can be interpreted loosely as a probability or confidence estimate that Xk is a member of the output set Yn (e.g. that the sample of echo signals correspond to a set of pixel image data). The output sets, Yn, can also represent numerical value ranges. In this manner, a set of RF signals may be provided as input to the neural network 160, the set of RF signals corresponding to a subset of a given spatial locations (e.g., a region of interest in the imaged tissue) within the medium and the neural network may provide as output a set of corresponding pixel data for producing a portion of the image at the given spatial location. In some examples, by changing the weights of the neural network, this system can be dynamically reconfigured to produce images of a wide variety of different characteristics. In some embodiments, the neural network 160 may be a deep-learning or simply deep neural network (DNN) and/or an adaptive neural network. In some embodiments, a deep neural network (DNN), such as a deep convolutional neural networks (deep CNN) also referred to as fully convolutional network (FCN), may be used to localize objects within an image on a pixel by pixel basis. In examples, the input training arrays, Xi, may be formed from any desired type of image data (e.g., flow image data, elastography image data) surrounding point in a region of interest in an image. Each training array may be classified into one or more output sets or values based on the set membership of the output point or pixel in question. As such, the ultrasound system 100 may be configured to at least partially bypass certain conventional signal processing to output imaging data for producing ultrasound images, in some cases in combination with echo intensity information derived through conventional signal processing. Rather, the estimation or prediction of values that form the imaging data output by the neural network would be accomplished implicitly within the neural network.

In examples of blood flow and/or contrast imaging, temporal aspects may be accounted for in the training of the neural network. If the ultrasonic echoes, ei, as shown in FIG. 3, are selected to include data acquired over multiple ultrasonic transmit receive cycles, then a training process as described herein may be used to distinguish different tissue types on the basis of the spatial and temporal characteristics of the echoes from multiple transmit events. In, such a manner, the neural network may be trained to produce imaging data associated with moving tissue (e.g., blood flow) and/or contrast media. Further, in examples of intravascular ultrasound (IVUS) imaging, such as when the neural network operates on echoes acquired from an array supported on an imaging catheter, the neural network may be trained to identify and localize flowing flood from the 2D echo image data by training the neural network with per-channel echo data from multiple frames as training input (xi) and the corresponding segmented (in some cases manually) image data (tissue/blood) as training output (yi). Echo signals and/or beamformed signals acquired over multiple transmit/receive cycles may be used for other blood flow or other moving tissue detection and imaging applications.

As described, the output of the neural network 160 may be coupled to the processor 150 for combining with imaging data produced by conventional signal processing techniques. For example, the output of the neural network 160 may be coupled to the scan converter 130 and multiplanar reformatter 132 and/or volume renderer 134 for arranging the subsets of pixel data received from the neural network, based on their spatial attributes, and presenting the imaging data in a desired format (e.g., a 2D or 3D ultrasound image). In some examples, the imaging data (e.g., pixel data) or tissue information provided by the neural network may be buffered until sufficient amount of pixel data, for example, enough to construct a full frame of a color flow, vector flow, or an elastography image, has been output by the neural network. In some examples, prior to passing the output data to the processor 150, the output of the neural network may be passed through a data conditioner 164, which may be configured to spatially and temporally process the output data to highlight certain spatial and/or temporal characteristics thereof. In some examples, the data conditioner 164 may be configured to perform multi-resolution image processing.

Once combined the imaging data produced by the neural network has been combined with that produced by processor 150, the data may be additionally processed, in conventional manner to enhance the final image and/or add annotation, as previously described. The ultrasound image(s) may be displayed in real-time, e.g., on a display unit of the user interface 124, buffered into a cineloop memory for displaying temporal sequences of images, and/or exported to a storage device or a printing system. Stored ultrasound images (or pre-formatted/pre-annotated imaging data) may be retrieved for subsequent analysis and diagnosis, inclusion in a report and/or for use as training data. The ultrasound imaging data may be further processed using conventional techniques to extract additional quantitative and/or qualitative information about the anatomy or characteristics of the tissue being scanned.

In some embodiments, the RF signals (e.g., from channel memory 110 or the beamformer memory) may be coupled to the neural network 160 via an input data selector 162. The input data selector 162 may be configured to select, for each point or region of interest (ROI) in an imaging field of view, a corresponding array of m RF signal samples (e.g., echo signal samples) from each or a subset of elements of the transducer array. In some examples, the input data selector 162 may be configured to select the samples such that the centers of the samples of RF signals correspond approximately to the round trip time delay and thus to the depth of interest (see e.g., FIG. 3). As shown in the example in FIG. 3, m samples of echo signals $e_i$ (i.e. per-channel data represented by $e_1, e_2, e_3, \ldots e_n$) are shown to have been selected based on having their centers corresponding to the depth of interest. In some examples, as long as the data segment lengths are long enough to include the information from each echo surrounding the depth of interest, it may not be strictly necessary to center the depth of interest within the echo segments. In some embodiments, the data selector 162 may thus be configured to select a subset of echo signals from the acquired echo signals, which are associated with adjacent points within a region of imaged tissue. After selection of the appropriate input data set, imaging and other tissue data extraction would be performed implicitly by the neural network 160 without the reliance on conventional beamforming.

In some examples, the neural network 160 may be trained to operate in a plurality of modes based, at least in part, on the input data type (e.g., per-channel data, beamformed signals, quadrature data, imaging data, or a combination thereof). For example, when using beamformed RF signals, select samples of the beamformed RF signals (over single or multiple transmit/receive cycles) may be coupled to the neural network 160, e.g., via an input data selector 162, which is configured to select the appropriate sample of beamformed RF signals corresponding to the ROI. In such examples, instead of or in addition to per-channel signals, the sample selector would select samples of RF signals corresponding to scanlines from the region of interest and as well as neighboring lines of sight, or they could may represent beamformed RF signals corresponding to scanlines generated from successive transmit events. Ultrasound imaging data for the scanlines corresponding to the input array of beamformed RF signals can thus be implicitly estimated by the neural network directly from the beamformed RF signals.

Figure 4:
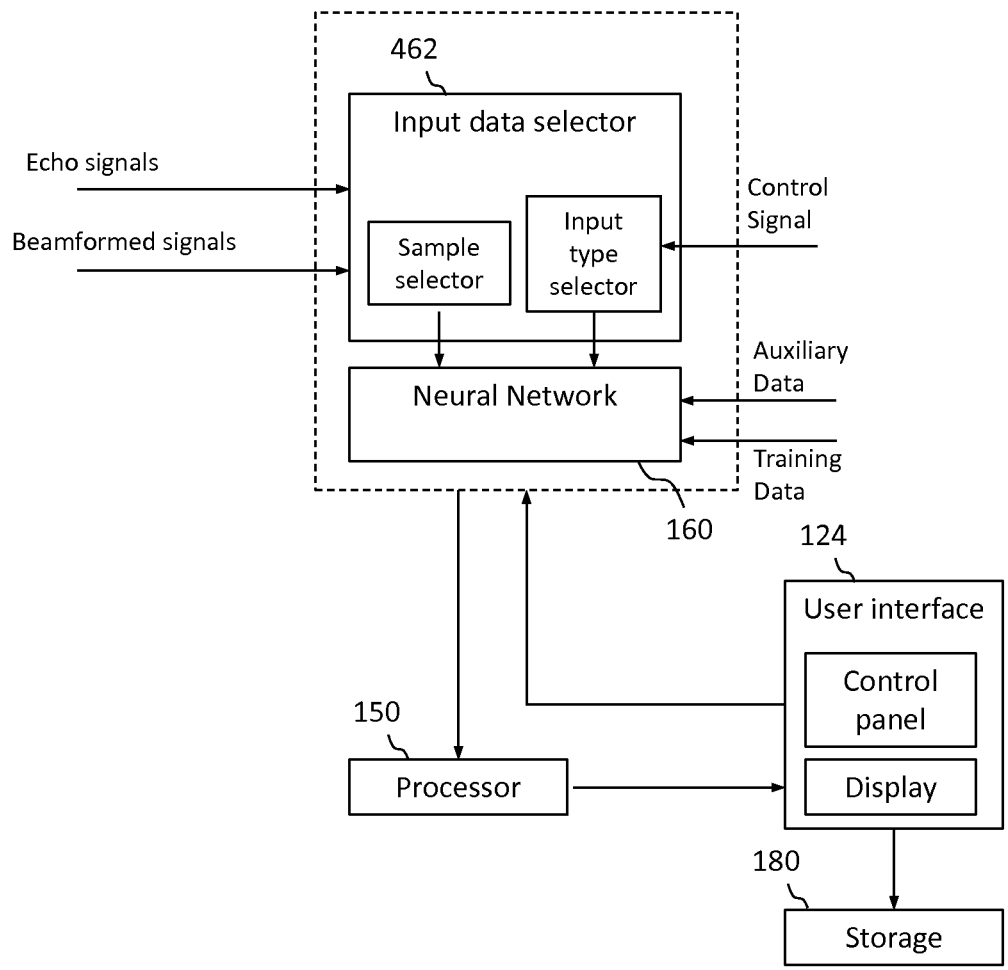
FIG. 4 shows a block diagram of an input data selector in accordance with principles of the present inventions.
Figure 5:
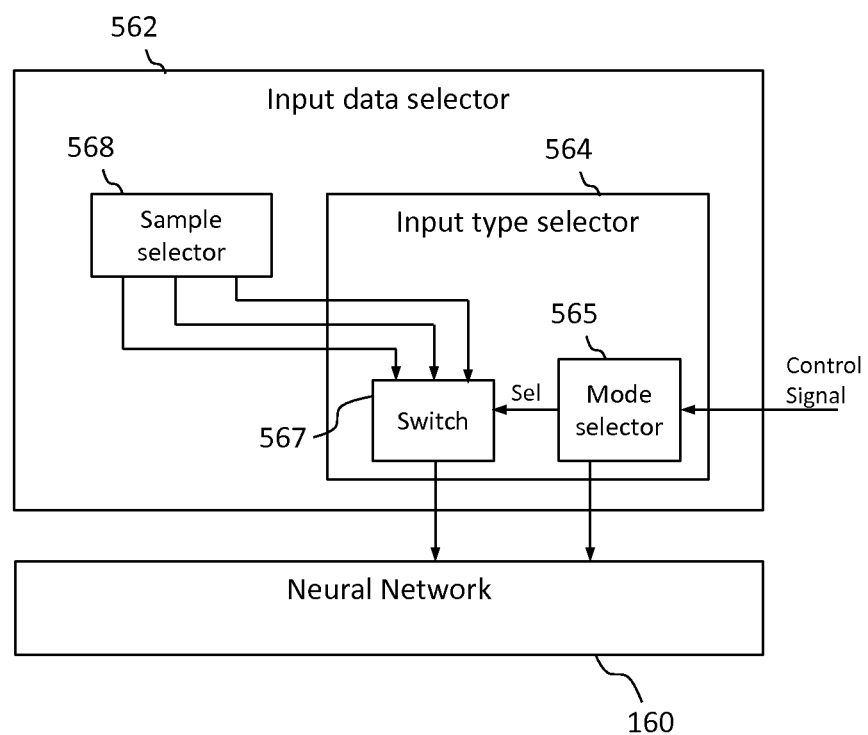
FIG. 5 shows another block diagram of an input data selector in accordance with further principles of the present inventions.

The input data selector 162 may be further configured to activate the appropriate operational mode of the neural network 160, which may be responsive to user input or which may be a pre-programmed default based on the imaging mode during acquisition of the echo signals (e.g., flow imaging, elastography, etc.). FIGS. 4 and 5 show examples of input data selectors 462 and 562 which may be operatively associated with neural network 160 to select the type and sample of input data and/or activate the appropriate mode of the neural network. The input data selector 462 or 562 may be used to implement the data selector 162 of the example system in FIG. 1.

For example, referring to FIG. 4, the input data selector 462 may include an input type selector which may selectively couple the type of data (e.g., echo signals or beamformed signals) to the neural network responsive to a control signal. The control signal may be generated based on user input. The input data selector 462 may include a sample selector which selects and couples the appropriate sample of signals of the selected type as previously described. To that end, and as shown in the example in FIG. 5, the input type selector 564 may include a mode selector 565 and a switch 567. The mode selector 565 may receive the control signal and send a select (Sel) signal to the switch to selectively couple the samples of the appropriate type of input data to the neural network 160. Additionally the input data selector 562 may be configured to activate the appropriate mode of the neural network, for example by transmitting a mode control signal (e.g., from the mode selector 565) to the neural network 160.

In some embodiments, the neural network 160 may be trained to operate in one or a plurality of different modes further based on the type of imaging data or tissue information that may be desired to be obtained. As described, the neural network 160 may be configured to output different types of imaging data responsive to the same input. For each of these different types of imaging data or tissue information, the network may be trained and thus include different propagation paths (e.g., layers of nodes and connection developed through appropriate training) and the propagation path or mode may be selected by the user or automatically invoked by the system depending on the imaging mode or application (e.g., blood flow imaging, fetal ultrasound imaging, etc.)

In some embodiments, the neural network of an ultrasound system according to the present disclosure may be configured to perform ultrasonic tissue characterization, for example to characterize fat content, plaque, or for ultrasonic contrast imagining, e.g., by presenting the neural network during a training phase with appropriate training data sets of inputs and known outputs, for example obtained through conventional ultrasound imaging or through imaging using a different modality.

For example, in ultrasonic liver imaging, ultrasonic attenuation and back-scattering (i.e., tissue echogenicity) increases in proportion to fat content while speed of ultrasound correspondingly reduces. By quantifying the ultrasound attenuation, echogenicity and/or speed from the beamformed RF echoes and correlating this attenuation with fat content, estimates of the fat content of the liver (or other tissue or organs, in other applications) may be performed with ultrasound. The customer-facing output of such a system may be quantitative (e.g., a single value representing the fat fraction within the imaged tissue), which may be displayed onto an image of the anatomy (e.g., for a specific point or region of interest) or it may be graphically represented, with each quantitative value being color-coded and overlaid on a 2D image or a 3D volume rendering of the liver (or other organ or tissue) similar to conventional overlays of blood flow or elastography information. As described, a neural network To train a neural network to extract tissue information pertaining to tissue content (e.g., fat content), the neural network may be presented with training data sets including localized raw RF signals and/or beamformed RF signals as inputs and the corresponding quantified tissue parameter (e.g., fat content or other type of tissue content), which may be obtained via the ultrasound quantification method above or through other imaging or non-imaging process capable of determining the tissue content of the tissue being imaged, as the known output. Once appropriately trained, the neural network may be opearable to implicitly extract this information directly from the raw RF signals and/or beamformed RF signals without reliance on the ultrasound quantification method used to initially obtain the training data.

In another example, plaque characterization may be enhanced by a neural network appropriately trained to replace existing vessel tissue classification models that are preprogrammed in conventional ultrasound systems, such as may be used by intravascular ultrasound (IVUS) catheters to provide colorized tissue map of plaque composition with lumen and vessel measurements. For example, the VH algorithm provided by Philips Volcano can be said to generally utilize beamformed ultrasound RF signals from an IVUS catheter and analyze the short-time windowed RF spectral properties of these echo signals to classify the tissue into one of several different categories such as fibrous tissue, necrotic core, dense calcium and fibro-fatty tissue. An image may then be provided showing the distribution of these tissue types within a vessel wall. Thus, to train the neural network of a system according to the present disclosure to provide relevant vessel tissue classification information, training data sets including IVUS-obtained RF signals may be provided as input with corresponding known tissue classifications (e.g., fibrous, necrotic core, dense calcium, etc.) as known outputs during a training phase of the neural network. Generally, raw RF signals and/or beamformed RF signals and corresponding vascular pathology data obtained using an existing IVUS system may be used to train an ultrasonic imaging system with a neural network to estimate vascular tissue composition directly from the detected echoes and/or beamformed signals, without the need for Fourier transforms and heuristic techniques that may currently be employed by conventional IVUS systems.

In yet further examples, the neural network may be trained to characterize tissue with respect to the presence of ultrasonic contrast agents. In ultrasonic contrast imaging, per-channel data from multi-pulse sequences (e.g. power modulation) are typically beamformed and then combined to form an image representing the volume density of microbubble contrast agents across the imaging field of view. The same may be implicitly (without beamforming and/or explicitly calculating the volume density) be achieved by a neural network which is trained with input training data in the form of per-channel data and/or at least partially beamformed data and corresponding known volume density of microbubble contrast agents.

In further examples, human hearts from multiple test subjects could be scanned using 1D or 2D array transducers and the resulting images and/or 3D volumes could be segmented (manually or automatically) into regions that are either a) within a cardiac chamber; or b) comprising myocardial tissue. These images may be used to train the neural network 160 to perform cardiac chamber recognition. In examples, the input data, [xi], may be per-channel data and optionally auxiliary data as described herein, while the output data would be a classification (i.e., either a) or b). In examples, the neural network may include an appropriately trained semantic classifier to perform this type of classification. The so trained neural network may then be used to segment and identify cardiac chambers directly from the raw or beamformed data without having to first reconstruct an image of the anatomy and without reliance on image processing techniques. This segmentation information could be used to suppress imaging artifacts, or it could be fed directly into algorithms to quantify ejection fraction or other clinical parameters. The system may be similarly trained to identify other types of tissue or anatomical structures (e.g., walls of vessels, lung/pleura interface) and quantify relevant clinical parameters associated therewith (e.g., obtain a nuchal translucency measurement).

As shown in the examples in FIGS. 1 and 4, the neural network may be configured to receive auxiliary data, such as information about the programming of the beamformer 122, properties of the transducer 113 (e.g., number, arrangement, and/or spacing of elements of the array, type of array, etc.), known information about the anatomy being imaged, and/or the spatial location of the point or region of interest (e.g., as may be obtained by a transducer tracking system). Other types of information, for example in the case of training sets from different imaging modalities, may also be provided as auxiliary information to the training algorithm. In some embodiments, the neural network may receive auxiliary data may be used during the training process to supplement the training data sets. Optionally, auxiliary data may also be provided to the neural network during an imaging session.

Figure 6:
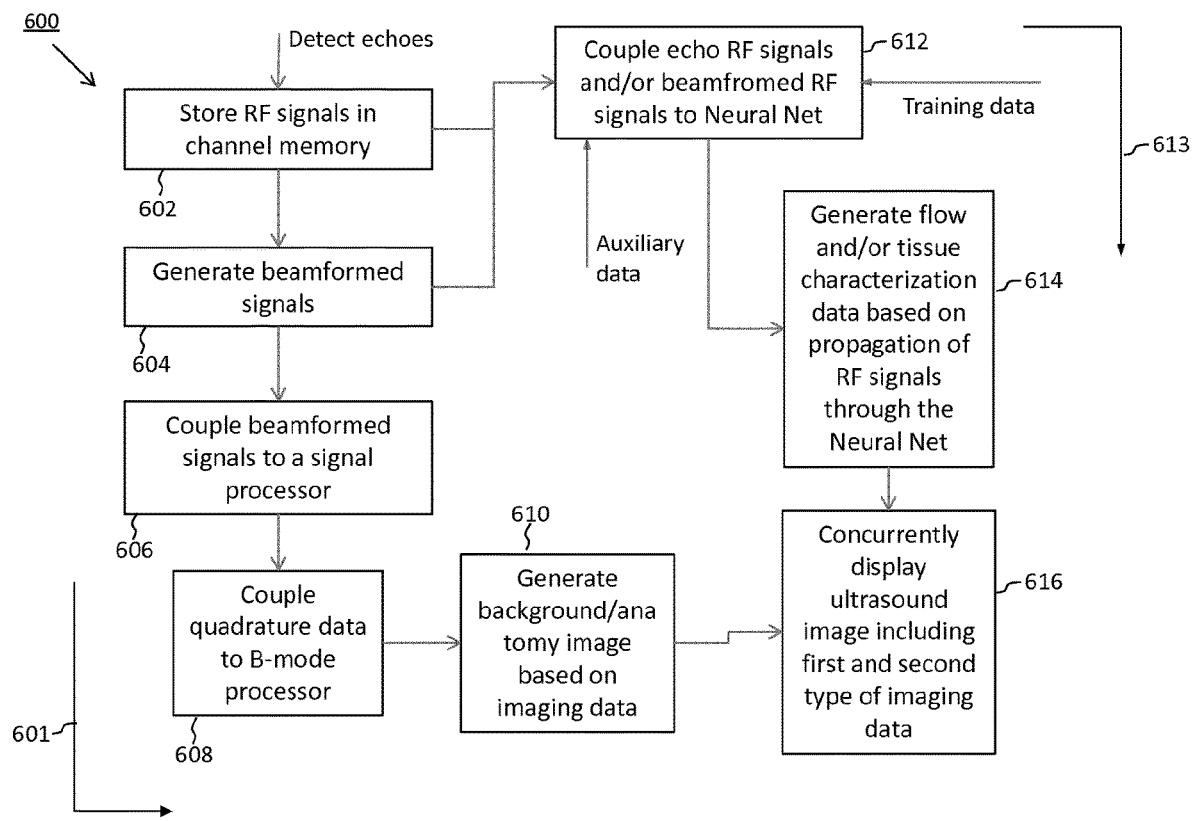
FIG. 6 is a flow diagram of a process of producing ultrasound images in accordance with the principles of the present inventions.

FIG. 6 shows a flow diagram of a process in accordance with some examples of the present disclosure. The process 600 may begin by storing the acquired echo RF signals in channel memory, as shown in block 602. The RF signals stored in channel memory correspond to the echoes detected from the tissue being image response to ultrasound transmitted by a transducer (e.g., transducer 113) operatively coupled to an ultrasound system (e.g., system 100). In some embodiments, the method may include generating beamformed RF signals based on the echo signals, as shown in block 604. The beamformed signals may be generated by conventional beamforming techniques, for example using beamformer 122 of system 100. In some embodiments, beamformed RF signals from one or multiple temporally sequential transmit/receive cycles, may be stored in beamformer memory. The beamformed signals may be coupled to one or more signal and image processors (e.g., processor 150). For example, the beamformed signals may be coupled, as shown in block 606, to a signal processor for extracting quadrature data (i.e., I/Q components of the signal) which can be coupled, as shown in block 608 to a B-mode processor for generating an anatomy image (see block 610).

Samples of the echo RF signals and/or beamformed RF signals may be coupled to a neural network (e.g., neural net 160), as shown in block 612, and may then propagate through the layers of the network to produce imaging data or any type of tissue information depending upon the training and/or operation mode of the network. That is, in some embodiments, one type of imaging data may be obtained through conventional signal processing (e.g., signal processing path 601) and another type of imaging data may be obtained through implicit or predictive analysis of the input data (e.g., along neural network path 613) directly from the raw RF signals or beamformed RF signals, as shown in block 612. In some examples, the neural network may be deep neural network (DNN) or a convolutional neural network (CNN), which may be implemented in hardware (e.g., nodes corresponding to hardware components) or software (e.g., where nodes are represented using computer code). In some embodiments, the coupling of samples of raw or beamformed RF signals may be selective, e.g., responsive to user input or automatically controlled by the system based on the imaging mode or clinical application. The neural network may be trained to operate in a plurality of different modes each associated with a type of input data (e.g., raw channel data or beamformed data), and thus a corresponding operational mode of the neural network may be selected (automatically or responsive to user inputs) based on the type of input data to the neural network. The imaging data and/or tissue information output by the neural network may include B-mode imaging data, Doppler imaging data, vector flow imaging data, strain imaging data, wall As shown in block 616, ultrasound images, which include both the first type of imaging data and the second type of imaging data, may be produce and displayed on a display unit operatively associated with the ultrasound system.

In some embodiments, the neural network may also receive auxiliary data for use in producing the imaging data. During an operational mode, the neural network, which may be associated with a training algorithm, may receive training data sets, for example image data or other known information produced by the system itself (e.g., obtained by processing echo signals along path 601) or from other imaging systems which may or may not utilize ultrasound as the imaging modality.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. An ultrasound system comprising:
   an ultrasound transducer configured to transmit ultrasound pulses toward tissue and generate echo signals responsive to the ultrasound pulses;
   a channel memory configured to store the echo signals;
   a beamformer configured to generate beamformed radiofrequency (RF) signals responsive to the echo signals;
   a neural network configured to receive input data comprising one or more samples of the echo signals or the beamformed RF signals and produce a first type of ultrasound imaging data;
   a processor configured to generate a second type of ultrasound imaging data based on the beamformed RF signals, wherein the processor is further configured to generate an ultrasound image based on the first type of ultrasound imaging data and the second type of ultrasound imaging data; and
   a data selector configured to select a subset of the stored echo signals or the beamformed RF signals as the one or more samples for input to the neural network.

2. The ultrasound imaging system of claim 1, wherein the second type of ultrasound imaging data comprises B-mode imaging data, and wherein the first type of ultrasound imaging data comprises one of Doppler imaging data, vector flow imaging data, elastography imaging data, tissue type characterization data, wall shear stress of an anatomical structure containing a fluid therein, tissue composition data, ultrasound contrast agent information, plaque characterization data, one or more diagnostic indicators associated with the B-mode imaging data, or combinations thereof.

3. The ultrasound system of claim 1, wherein the neural network includes a deep neural network (DNN) or a convolutional neural network (CNN).

4. The ultrasound imaging system of claim 1, wherein the neural network is implemented, at least in part, in a computer-readable medium comprising executable instructions, which when executed by a neural network processor coupled to the channel memory, the beamformer, or both, cause the neural network processor to perform a machine-trained algorithm to produce the first type of ultrasound imaging data responsive to the one or more samples of the echo signals or the beamformed RF signals.

5. The ultrasound imaging system of claim 1, wherein the data selector is configured to selectively couple one of the sample of echo signals or the sample of the beamformed RF signals to the neural network responsive to a control signal received by the data selector.

6. The ultrasound imaging system of claim 1, further comprising a display, and wherein the processor is further configured to cause the display to display the ultrasound image.

7. The ultrasound imaging system of claim 1, wherein the neural network is further configured to receive auxiliary data as input, the auxiliary data including ultrasound transducer configuration information, beamformer configuration information, information about the medium, or combinations thereof, and wherein the first type of ultrasound imaging data provided by the neural network is further based on the auxiliary data.

8. The ultrasound imaging system of claim 1, wherein the neural network is operatively associated with a training algorithm configured to receive an array of training inputs and known outputs, wherein the training inputs comprise echo signals, beamformed RF signals, or combinations thereof associated with a region of imaged tissue and the known outputs comprise known properties of the imaged tissue.

9. The ultrasound imaging system of claim 8, wherein the known properties are obtained using an imaging modality other than ultrasound.

10. The ultrasound system of claim 1, wherein the neural network is configured to process the input data in accordance with one of a plurality of operational modes, which is selected responsive to user input or automatically set by the ultrasound system based on an imaging mode of the ultrasound system during acquisition of the echo signals.

11. The ultrasound system of claim 1, wherein the neural network is configured to predict a fat content of the tissue based on the input data without use of the second type of imaging data.

12. The ultrasound system of claim 1, wherein neural network is configured to predict flow properties of a fluid contained in an anatomical structure of the tissue based on temporally successive samples of the input data without the use the quadrature signals produced by the image processing circuit.

13. The ultrasound system of claim 1, wherein the neural network is configured to produce predicted beamformed signals based on samples of the echo signals, and to use the predicted beamformed signals to generate the first type of imaging data.

14. An ultrasound system comprising:
   an ultrasound transducer configured to transmit ultrasound pulses toward tissue and generate echo signals responsive to the ultrasound pulses;
   a channel memory configured to store the echo signals;
   a beamformer configured to generate beamformed radiofrequency (RF) signals responsive to the echo signals;
   a neural network configured to receive input data comprising one or more samples of the echo signals or the beamformed RF signals and produce a first type of ultrasound imaging data, wherein the neural network is further configured to receive auxiliary data as input, the auxiliary data including ultrasound transducer configuration information, beamformer configuration information, information about the medium, or combinations thereof, and wherein the first type of ultrasound imaging data provided by the neural network is further based on the auxiliary data; and
   a processor configured to generate a second type of ultrasound imaging data based on the beamformed RF signals, wherein the processor is further configured to generate an ultrasound image based on the first type of ultrasound imaging data and the second type of ultrasound imaging data.

15. The ultrasound imaging system of claim 14, wherein the second type of ultrasound imaging data comprises B-mode imaging data, and wherein the first type of ultrasound imaging data comprises one of Doppler imaging data, vector flow imaging data, elastography imaging data, tissue type characterization data, wall shear stress of an anatomical structure containing a fluid therein, tissue composition data, ultrasound contrast agent information, plaque characterization data, one or more diagnostic indicators associated with the B-mode imaging data, or combinations thereof.

16. The ultrasound imaging system of claim 14, further comprising a data selector configured to select a subset of the stored echo signals or the beamformed RF signals as the sample for input to the neural network.

17. The ultrasound system of claim 14, wherein the neural network is configured to process the input data in accordance with one of a plurality of operational modes, which is selected responsive to user input or automatically set by the ultrasound system based on an imaging mode of the ultrasound system during acquisition of the echo signals.

18. An ultrasound system comprising:
an ultrasound transducer configured to transmit ultrasound pulses toward tissue and generate echo signals responsive to the ultrasound pulses;
a channel memory configured to store the echo signals;
a beamformer configured to generate beamformed radiofrequency (RF) signals responsive to the echo signals;
a neural network configured to receive input data comprising one or more samples of the echo signals or the beamformed RF signals and produce a first type of ultrasound imaging data, wherein the neural network is configured to process the input data in accordance with one of a plurality of operational modes, which is selected responsive to user input or automatically set by the ultrasound system based on an imaging mode of the ultrasound system during acquisition of the echo signals; and
a processor configured to generate a second type of ultrasound imaging data based on the beamformed RF signals, wherein the processor is further configured to generate an ultrasound image based on the first type of ultrasound imaging data and the second type of ultrasound imaging data.

19. The ultrasound imaging system of claim 18, wherein the second type of ultrasound imaging data comprises B-mode imaging data, and wherein the first type of ultrasound imaging data comprises one of Doppler imaging data, vector flow imaging data, elastography imaging data, tissue type characterization data, wall shear stress of an anatomical structure containing a fluid therein, tissue composition data, ultrasound contrast agent information, plaque characterization data, one or more diagnostic indicators associated with the B-mode imaging data, or combinations thereof.

20. The ultrasound imaging system of claim 18, further comprising a data selector configured to select a subset of the stored echo signals or the beamformed RF signals as the sample for input to the neural network.

* * * * *